US00PP31991P3

(12) United States Plant Patent
Giacomelli et al.

(10) Patent No.: US PP31,991 P3
(45) Date of Patent: Jul. 21, 2020

(54) RASPBERRY PLANT NAMED 'DAFNE'

(50) Latin Name: ***Rubus idaeus* L.**
Varietal Denomination: Dafne

(71) Applicant: SANT'ORSOLA SOCIETA' COOPERATIVA AGRICOLA, Pergine Valsugana (IT)

(72) Inventors: Sara Giacomelli, Vigolo Vattaro (IT); Loris Osti, Tocegno (IT); Marco Giacomelli, Vigolo Vattaro (IT); Alessandra Viliotti, Vigolo Vattaro (IT)

(73) Assignee: SANT'ORSOLA SOCIETA' COOPERATIVA AGRICOLA, Pergine Valsugana (IT)

( * ) Notice: Subject to any disclaimer, the term of this patent is extended or adjusted under 35 U.S.C. 154(b) by 0 days.

(21) Appl. No.: 16/350,828

(22) Filed: Jan. 18, 2019

(65) Prior Publication Data

US 2019/0223341 P1 Jul. 18, 2019

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./156, 203, 204
See application file for complete search history.

*Primary Examiner* — Susan McCormick Ewoldt
(74) *Attorney, Agent, or Firm* — Pepper Hamilton LLP

(57) ABSTRACT

A new a primocane raspberry cultivar named 'Dafne' which produces glossy, strong red firm fruits is disclosed, with berries which are easy to pick due to low adherence to the plug. The new cultivar has the advantages of producing two crops per year, wherein the fruits equally ripen on the current season's cane in autumn and on the previous year's cane in summer.

4 Drawing Sheets

Genus and species: *Rubus idaeus* L.
Variety denomination: 'Dafne'.

BACKGROUND OF THE NEW VARIETY

A new and distinct cultivar of red raspberry (*Rubus idaeus* L.) hereinafter referred to by the cultivar denomination 'Dafne' is disclosed. The new variety 'Dafne' was obtained from open pollination of the variety 'Amaranta' (mother plant) (not patented) and an unknown father plant pollen.

The crossing for the new cultivar occurred in year 2012 in Altopiano della Vigolana (Trento-Italy) and it was subjected to selection in 2013, and successively tested until 2017. The characteristics of the new cultivar have been found stable and have been transmitted without change through succeeding (more than 5 years) asexual propagations by root cutting.

Plant breeder's rights were applied for with the European Union on Jan. 18, 2018. 'Dafne' has not been made publicly available.

SUMMARY OF THE INVENTION

The most outstanding and distinguishing characteristics of the cultivar 'Dafne' are hereunder reported.

Primocane raspberry plant;
Good fruit colour and flavour;
Glossy strong red firm fruit;
Easy to pick up (low adherence to plug).

The new variety produces two crops per year and the fruits mainly ripen on current season's cane in autumn.

The new variety can be propagated by: the use of suckers produced in a spawn-bed, root cutting and use of tissue culture techniques. The root cutting is to be preferred.

BRIEF DESCRIPTION OF THE PHOTOGRAPHS

The new red raspberry cultivar 'Dafne' is illustrated by the accompanying photographs showing typical specimens of the new variety in colour as true as reasonably possible to make the same colour illustrations of this character by conventional photographic procedures. The photographs are of plants that are from four to six months old.

DETAILED DESCRIPTION

Figure 1:
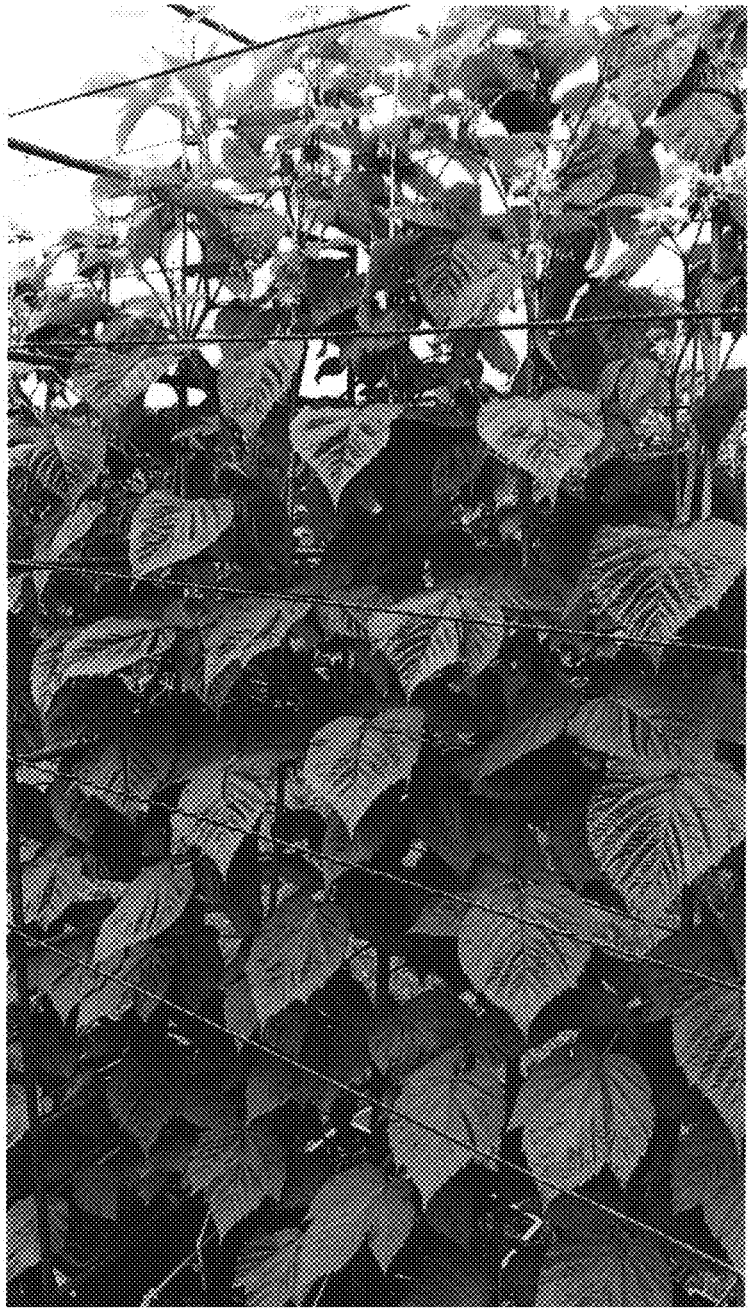
FIG. 1 is a view showing the upright, tall and vigorous raspberry plants during the flowering.
Figure 2:
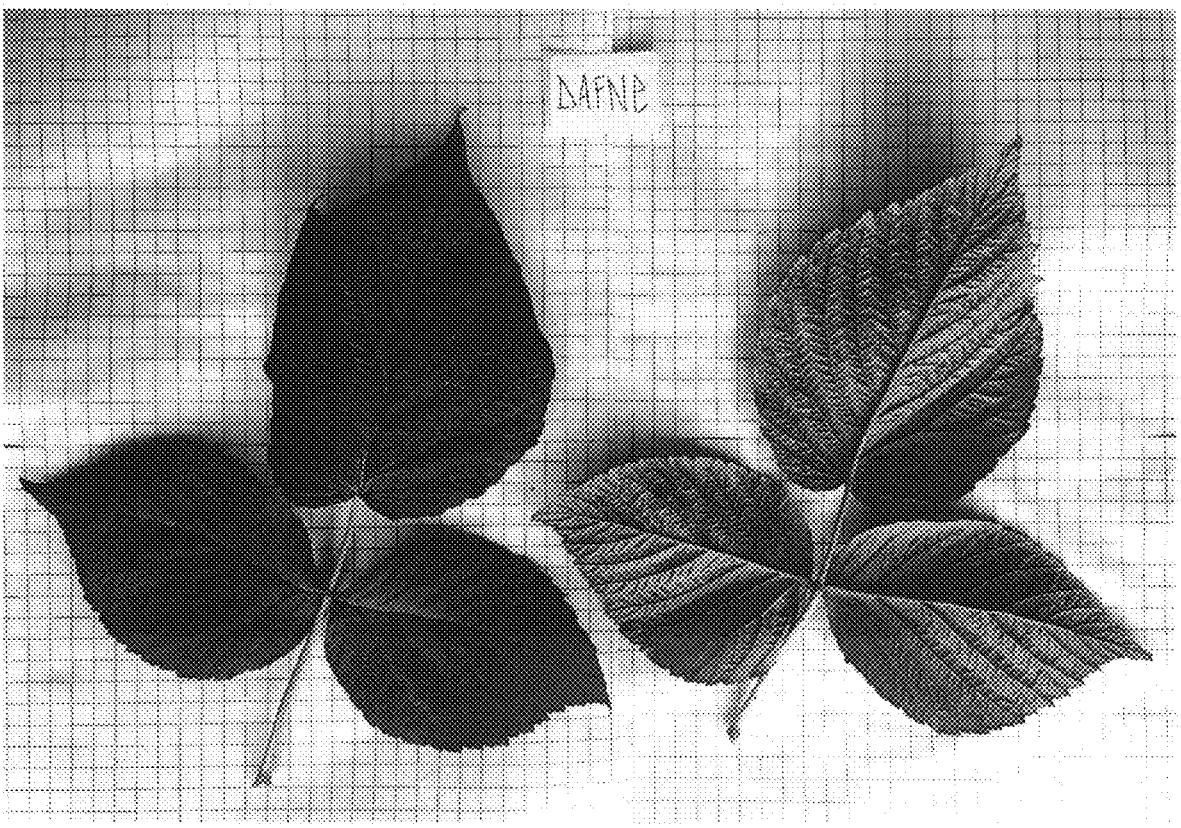
FIG. 2 is a view showing the leaf upper and lower surfaces.
Figure 3:
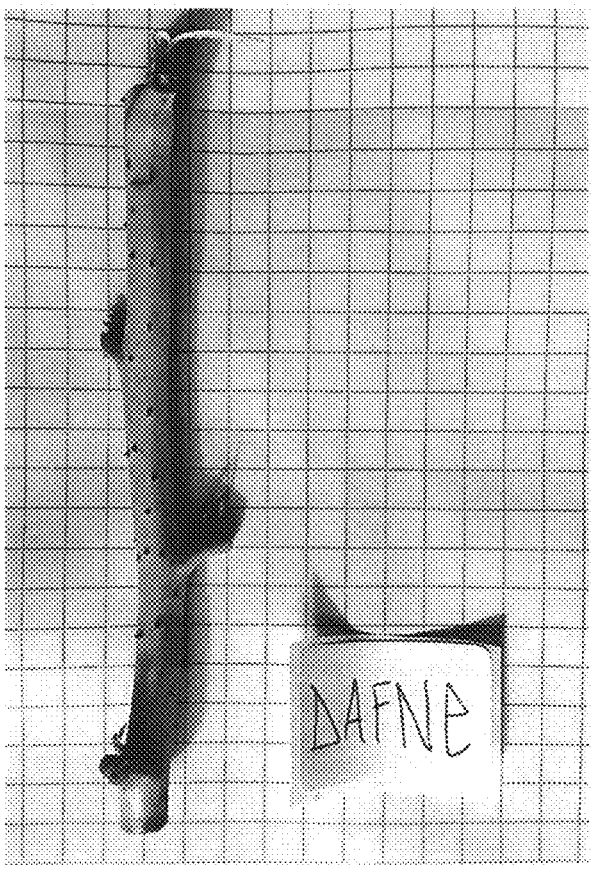
FIG. 3 is a view showing the plant primocane internode length, cane colour and thorns.
Figure 4:
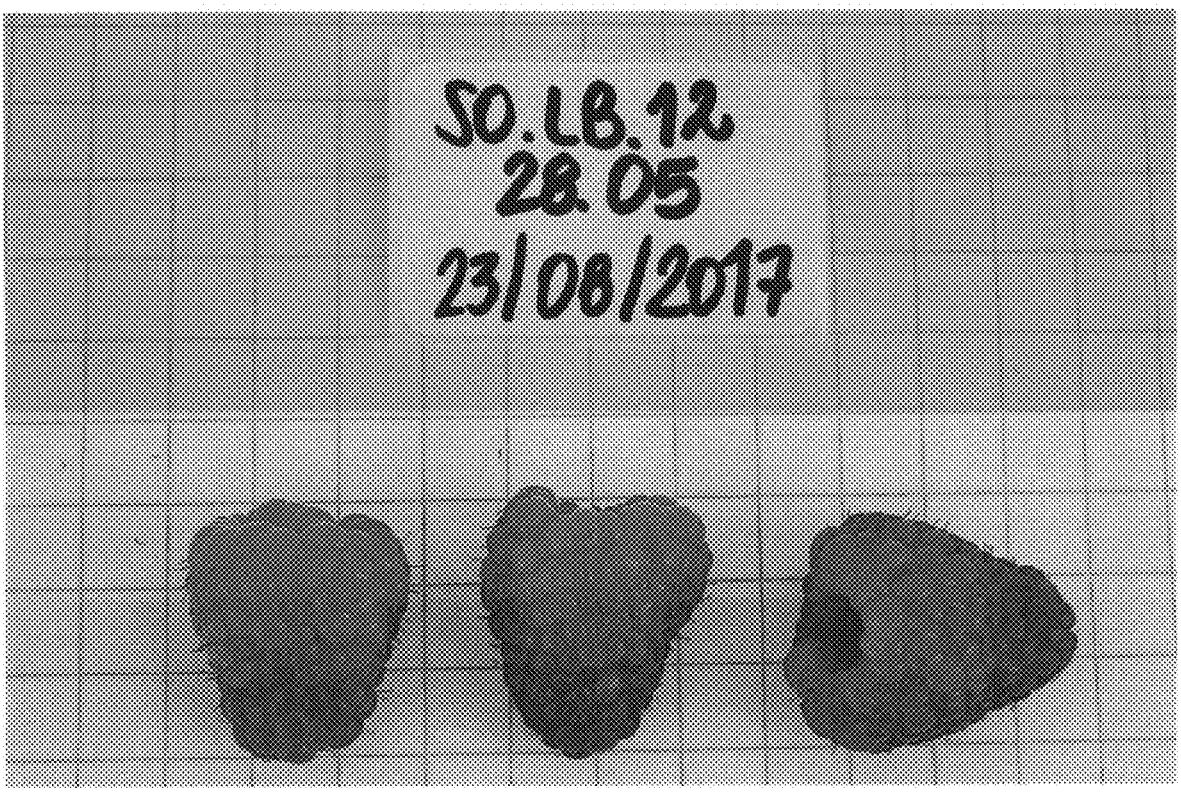
FIG. 4 is a view showing the ripe fruit size and shape.

The following detailed description set forth the distinctive characteristics of the new variety 'Dafne'. The performance of the new cultivar for retention of its distinctive characteristics has been evaluated through successive asexual propagations by root cutting in the Applicant's setting in Altopiano della Vigolana, Trentino Region (Italy) under natural conditions in plastic covered high tunnels. The growing was in soilless conditions using coir as substrate.

The plant assessment was performed for 2 years. Botanical descriptions are for plants 16-18 months old.

* Colour references made to R.H.S. Colour Chart of The Royal Horticultural Society of London (Edition V)

Classification:

*Family*.—Rosaceae.
*Botanical*.—*Rubus idaeus* L.
*Common name*.—Raspberry.

Parentage: 'Amaranta' (mother) x unknown pollen (father).

Plant:

*General habit*.—Upright canes; strong vigor; very good roots system; adapted to medium winter chill conditions such as those at Altopiano della Vigolana (average min temperature 1° C.; average max temperature 5° C.); quite resilient to summer heat (average min temperature 13° C.; average max temperature 27° C.). Suitable for being harvested both on current year's cane in autumn and on previous year's cane in summer.

*Average height* (*average*).—1.70-1.80 m.

*Spread* (*average*).—0.80 m.

*Shape*.—Conical.

*Vegetative bud length*.—6.0-8.0 mm.

Primocane:

*Length* (*average*).—1.70-1.80 m.

*Diameter* (*average*).—1.0 cm.

*Texture*.—Smooth.

*Internode length* (*average*) *at* 1 *m height*.—5-6 cm.

*Number of fruiting laterals per cane* (*average*).—9.

*Number of current season's shoots*.—Medium.

*Young shoot colour*.—*RHS:144A.

*Cane colour*.—*RHS: N144C.

*Spines*.—Present.

Floricane:

*Dormant cane colour*.—*RHS: 72A.

*Fruiting lateral attitude in summer*.—Semi erect.

Spines:

*Shape*.—'Shark fin'.

*Size* (*average*).—1.50-1.70 mm.

*Density* (*average*) *at* 1.2 *m height*.—2.3-2.5 $cm^2$.

*Colour*.—*RHS N77A.

Foliage:

*Leaves*.—Shape: compound; odd-pinnate and subdivided in 3 cordate and serrate. Profile in cross section: slightly convex. Rugosity: medium. Complete leaft: Length: 34.2 cm. Width: 31.5 cm. Upper surface colour *RHA 141A. Lower surface colour *RHS 147D. Lateral leaflets: specular. Lateral leaflets average size: length: 15.4 cm. Width: 11.2 cm. Lateral leaflets apex shape: pointed. Lateral leaflets base shape: ovate. Lateral leaflets margin type: serrate. Terminal leaflets average size: length: 16.9 cm. width: 14.5 cm. Terminal leaflets apex shape: pointed. Terminal leaflets base shape: cordate. Terminal leaflets margin type: serrate.

*Petiole*.—Average length: 10.8 cm. Average diameter: 0.5 cm. Colour: *RHS 143D.

Inflorescence:

*Average length*.—40.5 cm.

*Average diameter*.—33 cm.

Flowers:

*Number per plant* (*average*).—Primocane: 160. Floricane: 195.

*Length* (*average*).—9.66 mm.

*Diameter* (*average*).—34.79 mm.

*Diameter* (*receptacle*).—11.29 mm.

*Shape*.—Pentagonal.

*Petal colour* (*upper surface*).—*RHS: NN155C.

*Petal colour* (*lower surface*).—*RHS: NN155C.

*Petal number* (*average*).—5.

*Petal shape*.—Obovate. Apex: rounded. Base: cuneate. Margin: entire.

*Sepal number* (*average*).—5. Colour (upper surface): *RHS: 144B. Colour (lower surface): *RHS: N144D. Length (average): 1.4 cm. Width (mid part): 0.7 cm.

*Fragrance*.—Absent.

*Blooming*.—Primocane: July-August. Floricane: April-May.

*Pedicel*.—Length (average): 2.6 cm.

Fruit:

*Predominant shape*.—Broad conical.

*Weight*.—6.3 g.

*Size*.—Length: 2.3 cm. width: 2.6 cm.

*Colour of ripe fruit*.—*RHS: 50A.

*Colour of immature fruit*.—*RHS: 52D.

*Firmness*.—Firm (0.05 Kg).

*Drupes per fruit* (*average*).—140.

*Drupe size*.—Length: 4.07 mm. width: 3.5 mm. depth: 6.2 mm.

*Glossiness*.—High.

*Adherence to plug*.—Low.

*Titratable acidity*.—32.00 meq/hg.

*Soluble solids*.—9° Brix.

*Harvest season*.—Primocane: August to October. Floricane: half June-end July.

*Autumn yield*.—4 kg/m (4 plants/m).

*Summer yield*.—4.9 kg/m (4 plants/m).

*Use/market*.—Suitable for consumption as high grade fresh fruit and also amenable to processing.

*Keeping quality*.—The fruit colour tends to become darker during storage, but the high glossiness makes it attractive.

*Storage capacity* (*shelf life*).—Very good shelf-life.

*Shipping quality*.—Good; the attitude to storability permits shipping.

Reproductive organs:

*Pistil number per flower* (*average*).—151.

*Pistil size* (*average*).—5.70 mm.

*Stamen number per flower* (*average*).—150.

*Stamen size* (*average*).—5.23 mm.

Seeds:

*Size* (*average*).—Length: 2.83 mm. width: 1.71 mm.

*Shape*.—Kidney-shaped.

Comparison with Commercial Cultivar

TABLE 1

Comparison table between variety and commercial cultivar Evita (U.S. Plant Pat, No. 25,695) and 'Lagorai Plus'(U.S. Plant Pat. No. 25,636)

| Characteristic | 'EVITA' | 'LAGORAI PLUS' | 'DAFNE' |
|---|---|---|---|
| fruit color | Orange red | Strong red | strong red |
| Fruit: glossiness | low | medium | high |
| Fruit shape | elongated conical, slight irregular | conical very regular | broad conical, very regular |
| Fruit picking | Slight difficult | Very easy | very easy |
| Autumn yield | high | low | medium |
| Summer yield | high | medium | |
| Dormant cane colour | purple-brown | moderate brown | greyish-purple |

TABLE 2

| Comparison table between variety and the female parent 'Amaranta' | | |
|---|---|---|
| Characteristic | 'Amaranta' (female parent) | 'Dafne' |
| Fruit color | Medium red | Strong red |
| Fruit shape | elongated conical | Broad conical, very regular |
| Fruit firmness | Soft to medium | firm |
| Autumn yield | Medium to high | medium |

TABLE 2-continued

| Comparison table between variety and the female parent 'Amaranta' | | |
|---|---|---|
| Characteristic | 'Amaranta' (female parent) | 'Dafne' |
| Summer yield | low | medium |
| Fruit: glossiness | Low | high |

What is claimed:

1. A new and distinct cultivar of raspberry plant as substantially herein shown and described.

* * * * *